United States Patent [19]

Ohta et al.

[11] Patent Number: 5,181,604

[45] Date of Patent: Jan. 26, 1993

[54] CONTACT LENS HOLDER AND TREATING DEVICE

[75] Inventors: Kiyohiko Ohta, Aichi; Kaoru Kamiya, Nagoya; Keiko Watanabe, Inazawa; Makoto Nakagawa, Aichi; Tomio Nagao, Gifu, all of Japan

[73] Assignee: Tomei Sangyo Co., Ltd., Japan

[21] Appl. No.: 756,883

[22] Filed: Sep. 9, 1991

[30] Foreign Application Priority Data

Sep. 14, 1990 [JP] Japan ................... 2-97121[U]

[51] Int. Cl.⁵ .......................................... A45C 11/04
[52] U.S. Cl. ........................ 206/5.1; 134/137; 134/901; 422/300
[58] Field of Search ............ 206/5, 5.1; 134/137, 134/158, 901; 422/300, 301

[56] References Cited

U.S. PATENT DOCUMENTS

| 3,939,698 | 2/1976 | Ryder | 206/5.1 |
|---|---|---|---|
| 3,997,049 | 12/1976 | Sherman | 206/5.1 |
| 4,011,941 | 3/1977 | Parson | 134/901 |
| 4,200,187 | 4/1980 | Thomas | 206/1.5 |
| 4,444,307 | 4/1984 | Jermyn . | |
| 4,700,729 | 10/1987 | Thaler | 134/901 |
| 4,750,610 | 6/1988 | Ryder | 206/5.1 |
| 4,807,750 | 2/1989 | Ryder | 206/5.1 |
| 4,826,001 | 5/1989 | Castillo . | |
| 4,889,693 | 12/1989 | Su et al. | 206/5.1 |
| 4,956,156 | 9/1990 | Kanner et al. | 206/1.5 |
| 4,957,130 | 9/1990 | Lee | 134/901 |
| 4,981,657 | 1/1991 | Ryder | 206/5.1 |
| 4,996,027 | 2/1991 | Kanner | 206/5.1 |
| 5,089,240 | 2/1992 | Perlaky | 422/300 |

FOREIGN PATENT DOCUMENTS

| 59-24015 | 7/1984 | Japan . | |
| 63-96533 | 6/1988 | Japan . | |
| 9014848 | 12/1990 | PCT Int'l Appl. | 422/301 |

Primary Examiner—David T. Fidei
Attorney, Agent, or Firm—Parkhurst, Wendel & Rossi

[57] ABSTRACT

A contact lens case including a cylindrical container body, a cap member for closing an opening of the container body, a support member which is attached at one end thereof to the cap member to extend therefrom in an axial direction of the container body, and a lens holder rotatably supported by the support member. The lens holder has one or more lens storage chamber each receiving the contact lens, and a plurality of holes which permit a liquid to flow therethrough. The present contact lens case further includes a detent structure for holding the lens holder selectively in a horizontal position in which the contact lens received in the holder has a horizontal attitude perpendicular to the axial direction of the container body, or in a vertical position in which the contact lens received has a vertical attitude parallel to the axial direction of the container body. Also disclosed is a lens treating device which uses the present contact lens case as an inner case that is axially slidden within an outer case for cleaning the contact lens stored therein.

12 Claims, 8 Drawing Sheets

CONTACT LENS HOLDER AND TREATING DEVICE

BACKGROUND OF THE INVENTION

1. Field of the Art

The present invention relates in general to a contact lens case for accommodating a contact lens or lenses, and a lens treating device which incorporates the lens case for treating the lenses. More particularly, the invention is concerned with such a contact lens case which may contain a suitable treatment liquid as well as the contact lenses, and is suitably used for cleaning, storing, sterilizing or otherwise treating the contact lenses. The invention is also concerned with such a lens treating device as described above, which permits considerably effective cleaning of the lenses.

2. Discussion of the Prior Art

Generally, after a contact lens for rectifying one's eyesight is removed from a human eye, the lens needs to be treated in suitable sequence, that is, cleaned, rinsed and stored. As for soft contact lenses, it is necessary to boil the lenses on a regular basis for the purpose of disinfection. Namely, there is a need to clean contact lenses so as to remove therefrom organic substances contained in tears, such as lipid, protein or glucide, and inorganic substances such as calcium or magnesium, which attach or adhere to the lenses during use.

As a method for cleaning the contact lenses, it has been proposed to use an exclusive cleaning container which may contain a cleaning liquid as well as the contact lenses, so as to clean the lenses by shaking the container. Examples of such a container are disclosed in Publication No. 59-24015 of examined Japanese Utility Model Application and laid-open Publication No. 63-96533 of unexamined Japanese Utility Model Application.

The cleaning container as described above is usually produced in a comparatively small size, so that the container may be easily shaked while being gripped by a hand. Therefore, the contact lenses must be put into and taken out of further smaller lens holders fixed in the small-sized cleaning container. Thus, handling the lenses is rather cumbersome in the known cleaning container.

To obtain a sufficiently high cleaning effect by using the cleaning container, the major surfaces of the contact lenses must be effectively exposed to the cleaning liquid which flows in the container while it is shaked by one's hand. To this end, the contact lenses are supported by or fitted in respective lens holders, and thus prevented from moving with the liquid flowing in the container.

However, the known cleaning container has not been able to produce a satisfactory result of cleaning the contact lenses supported by the holders, due to lack of consideration as to orientation or posture of the lenses with respect to the flows of the cleaning liquid during the cleaning operation. Generally, it is desirable that a contact lens be positioned in the cleaning container to have a horizontal attitude perpendicular to the direction of flows of the cleaning liquid, so that the lens can be most effectively cleaned.

The known cleaning containers as disclosed in the above-identified publications are unsatisfactory in solving the above-described problems, and suffer from difficulty in handling contact lenses, and insufficient cleaning of the lenses.

More specifically, in the cleaning container as disclosed in Publication No. 59-24015, a pair of contact lenses are held in respective lens holders which are fixed to inner surfaces of axially opposite lids. Accordingly, the lens holders may be taken out of the container when the lids are detached from the container. In this container, the contact lens must be inserted into a narrow slot (opening) of the lens holder so that the lens is held in the lens holder. Further, since the contact lenses are fixedly disposed in the container to have a vertical attitude parallel to the direction of flows of the cleaning liquid, the cleaning liquid is not sufficiently applied to the surfaces of the lenses, resulting in insufficient cleaning of the lenses.

In the cleaning container as disclosed in laid-open Publication No. 63-96533, a pair of contact lenses are fitted in respective narrow grooves formed in lens holders or receptacles. Therefore, the lenses are put into or taken out of the lens holders with some difficulty. Further, when the lens is put into and taken out of the container, the lens holders have to be taken out of the container, aside from opening the lids of the container, thus requiring a further cumbersome procedure to handle the lenses. Since the lens holders are adapted to be rotated and moved over a slight distance in the vertical direction in the container, the cleaning liquid is not sufficiently applied to the surfaces of the lenses, resulting in an insufficient effect of cleaning the lenses. The irregular rotary movements of the lens holder lead to an insufficient and uneven cleaning result. Furthermore, the container is rather complicated in construction, and easy to be broken.

The lens holders of the cleaning containers disclosed in the above publications are adapted to receive hard contact lenses. Namely, these lens holders cannot be used for soft contact lenses.

SUMMARY OF THE INVENTION

The present invention was developed in the light of the prior art situations described above. It is accordingly a first object of the invention to provide a contact lens case which may contain a contact lens or lenses and a suitable treatment liquid for cleaning, sterilizing, storing or otherwise treating the lens, and which enables the user to easily put the lens into and take the same out of the container. In the present lens case, the lens is positioned to have a horizontal attitude perpendicular to the direction of flows of a cleaning liquid during cleaning of the lens, so that the cleaning liquid is effectively applied to the surfaces of the lens, to accomplish effective cleaning of the lens.

It is a second object of the invention to provide a lens treating device which is able to effectively intensify the flows of the cleaning liquid which occur in the lens case during cleaning of the lenses, so as to obtain a further improved cleaning effect.

The first object may be attained according to one aspect of the present invention, which provides a contact lens case for accommodating a contact lens, comprising: (a) a cylindrical container body closed at one axial end, for receiving a liquid for treating the contact lens; (b) a cap member removably attached to the other axial end of the container body to fluid-tightly close an opening of the body, so that an enclosed space is defined between the cap member and the container body; (c) a support member which is attached at one end thereof to the inside of the cap member, and which extends from the cap member into the enclosed space in an axial direction of the container body; (d) a lens holder rotatably supported at the other end of the support member and accommodated in the enclosed space, the lens holder having at least one lens storage chamber each for receiving the contact lens, the lens holder having a plurality of through-holes which permit the liquid to flow therethrough; and (e) detent means disposed between the lens holder and the support member for preventing the lens holder from freely rotating in the enclosed space, and for holding the lens holder selectively in a horizontal position in which the lens holder has a horizontal posture substantially perpendicular to the axial direction of the container body, or a vertical position in which the lens holder has a vertical posture substantially parallel to the axial direction of the container body. The contact lens received in each lens storage chamber has a horizontal attitude substantially perpendicular to the axial direction of the container body when the lens holder is held in the horizontal position, and a vertical attitude substantially parallel to the axial direction of the container body when the lens holder is held in the vertical position.

In the contact lens case of the invention constructed as described above, the lens holder is selectively placed in one of the vertical and horizontal positions so that the contact lens(es) may be positioned in the lens holder to have the corresponding one of the vertical attitude parallel to the axial direction of the container body, and the horizontal position perpendicular to the same direction. When the lens holder is rotated to the vertical position and held in that position by the detent means, the contact lens can be easily put into or taken out of the lens holder, assuring significantly improved handling ease of the lens. If the contact lens is to be cleaned, the lens holder is rotated to and held in the horizontal position, so that the lens has the horizontal attitude perpendicular to the axial direction of the container body, that is, to the direction of flows of the cleaning liquid. As a result, the cleaning liquid flowing in the lens case is effectively applied to the contact lens to be cleaned, whereby a significantly improved cleaning effect can be obtained.

The second object may be attained according to another aspect of the present invention, which provides a lens treating device for treating a contact lens, comprising: (a) an elongate cylindrical outer case having a cylindrical body which is open at at least one of opposite axial ends, and at least one lid removably attached to the cylindrical body to close the at least one axial end thereof; and (b) the contact lens case as described above, as an inner case for fluid-tightly receiving the contact lens and a liquid for treating the contact lens, the inner case being accommodated in the outer case such that the inner case is axially slidingly reciprocable within the outer case, whereby the liquid is forced to flow within the inner case so as to clean the contact lens, by a reciprocating movement of the inner case when the outer case is axially shaken or repeatedly inverted. The detent means is adapted to hold the lens holder in the vertical position so that the contact lens received in the lens holder has the vertical attitude when the lens is put into or taken out of the lens holder, and to hold the lens holder in the horizontal position so that the contact lens has the horizontal attitude during cleaning of the contact lens.

The lens treating device constructed as described above enjoys all the advantages as described above with respect to the present contact lens case, since the device utilizes the contact lens case as the inner case to be accommodated in the outer case. When the inner case is axially slidingly reciprocated within the outer case, the liquid is caused to considerably intensely flow within the the inner case, due to shocks caused by collision of the inner case with the opposite axial ends of the outer case, even if the actual distance of movement of the outer case shaked by one's hand is relatively small. Thus, the instant lens treating device permits considerably effective cleaning of the contact lens.

BRIEF DESCRIPTION OF THE DRAWINGS

The above objects, features and advantages of the present invention will be better understood by reading the following detailed description of presently preferred embodiments of the invention, when considered in connection with the accompanying drawings, in which.

DETAILED DESCRIPTION OF THE PREFERRED EMBODIMENTS

Figure 1:
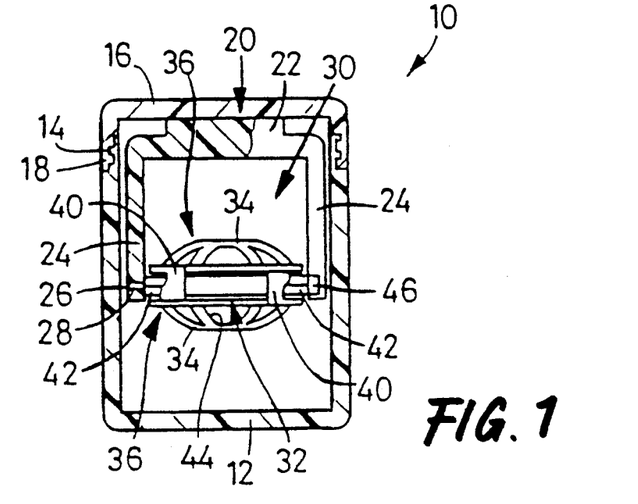
FIG. 1 is an elevational view in longitudinal cross section showing a contact lens case as one embodiment of the present invention.

Referring first to FIG. 1, there is shown one embodiment of the present invention in the form of a contact lens case 10 in which a pair of contact lenses can be accommodated. In FIG. 1, reference numeral 12 denotes a cylindrical container body which is closed at one axial end, and has an external screw-thread 14 formed on the outer circumferential surface of an open end portion thereof adjacent the other axial end. Reference numeral 16 denotes a cap member for closing the opening of the container body 12 so that an enclosed space is formed in the lens case 10. The cap member 16 has an internal screw-thread 18 formed on the inner circumferential surface of an open end portion thereof, which is adapted to engage the external screw-thread 14 of the container body 12 to ensure fluid-tightness of the lens case 10. It is to be understood that the container body 12 and the cap member 16 may be assembled together in any manners other than screwing, provided the fluid-tightness of the obtained lens case 10 is maintained.

Figure 2:
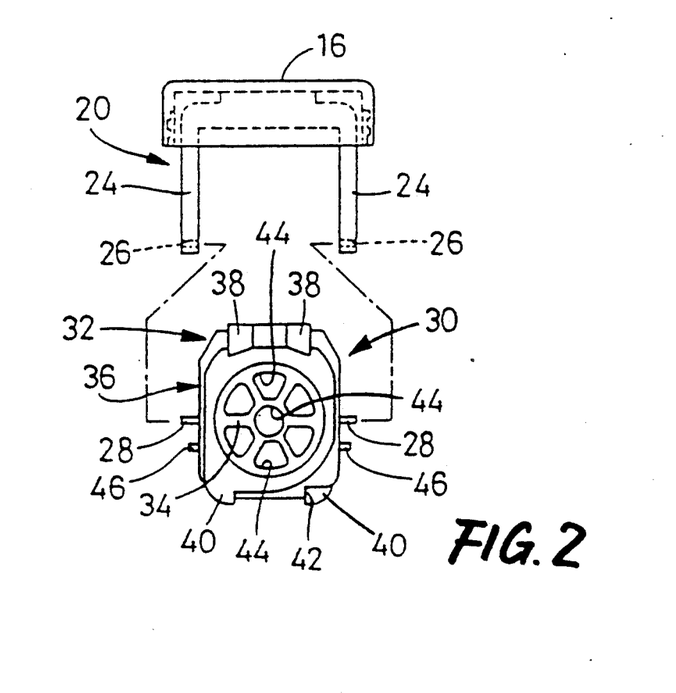
FIG. 2 is a view showing a cap member, a support member and a lens holder of the contact lens case of FIG. 1, before the lens holder is attached to the cap member via the support member.

In the enclosed space defined by the container body 12 and the cap member 16, there are provided a support member 20 secured to the inner surface of the bottom wall of the cap member 16, and a lens holder 30 supported by the support member 20. More specifically, the support member 20 is a generally U-shaped plate, and consists of a rear portion 22 having a length slightly smaller than the inside diameter of the cap member 16, and two arms 24 which extend from the opposite ends of the rear portion 22, in a direction perpendicular to the plane of the bottom wall of the cap member 16. The support member 20 is fixed at the rear portion 22 to the cap member 16, such that the arms 24 substantially protrude from the cap member 16, as shown in FIG. 2. With the container body 12 assembled with the cap member 16, the arms 24 of the support member 20 extend in the enclosed space in the axial direction of the container body 12, that is, in the vertical direction of the lens case 10. Each of the arms 24 has a through-hole 26 formed through its distal end portion remote from the rear portion 22. With two mounting rods 28 (which will be described below) of the lens holder 30 inserted into the respective through-holes 26 of the arms 24 of the support member 20, the lens holder 30 adapted to receive a pair of contact lenses is rotatably supported by the support member 20.

Figure 3:
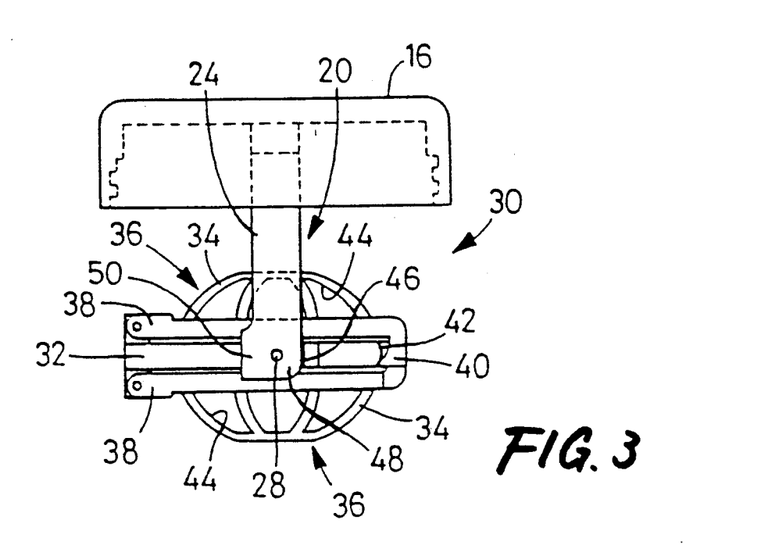
FIG. 3 is a side elevational view showing the lens case of FIG. 1, in which the lens holder is held in the horizontal position.

As shown in FIG. 2, the lens holder 30 includes a rotary member in the form of a rectangular rotary plate 32 with the mounting rods 28 formed integrally on respective intermediate parts of the opposite side faces thereof which are opposed to the arms 24 of the support member 20. On the opposite major surfaces of the rotary plate 32, there are respectively disposed rectangular pivotable members 36, 36, each having a basket portion 34 formed at its central part to provide a generally semispherical recess in which a contact lens is to be stored. The basket portions 34 of the pivotable members 36 cooperate with the rotary plate 32 to define therebetween two lens storage chambers for receiving a pair of contact lenses. Each pivotable member 36 has a hinge portion 38 which is formed at one side thereof where the member 36 is connected to the rotary plate 32. Namely, the pivotable members 36, 36 are pivotable about the axes of the hinge portions 38 with respect to the rotary plate 32. The pivotable member 36 further has a catch 40 formed on the side opposite to the hinge portion 38. The pivotable member 36 is held in a closed position as shown in FIGS. 1 and 3, with the catch 40 held in engagement with a cutout 42 formed in the rotary plate 32.

The basket portion 34 of each pivotable member 36 is dimensioned such that the largest diameter of the semispherical recess formed in the portion 34 is slightly larger than that of the contact lens to be accommodated therein, and such that the depth of the recess is slightly greater than the height of the contact lens. In this case, the contact lens accommodated in the basket portion 34 is kept in an initial posture with respect to the lens holder 30 such that the axis of the lens is substantially perpendicular to the plane of the rotary plate 32, even if the lens holder 30 is rotated as described later.

A plurality of holes 44 are formed through the basket portions 34 of the pivotable members 36, and through a portion of the rotary plate 32 which is aligned with the basket portions 34 held in their closed positions, so that a liquid in the lens case 10 can freely contact the contact lenses accommodated in the basket portions 34. It is to be understood that the size, shape and number of the holes 44 are not limited to those of the instant embodiment, but may be suitably changed as needed. For example, the above-indicated portions of the pivotable members 36 and rotary plate 32 are reticulated or provided with other forms of apertures, so that a suitable liquid, such as a cleaning liquid, may be passed through the apertures while preventing passage of the contact lenses therethrough.

The container body 12, cap member 16, support member 20, and lens holder 30 are formed of a material which is not affected by a cleaning liquid, for example, and which does not affect the cleaning liquid. In particular, these members 12, 16, 20, 30 are preferably formed of a synthetic resin, and more preferably, of an anti-bacterial resin material containing anti-bacterial zeolite, which is able to effectively prevent proliferation of bacteria or mold in the contact lens case 10.

On the side faces of the rotary plate 32 on which the mounting rods 28 are formed, there are also formed as integral parts two detent protrusions 46, respectively, which are spaced from the corresponding rods 28 by a suitable distance. On the other hand, each of the arms 24 of the support member 20 has a distal end portion as shown in FIG. 3, which faces the corresponding one of the above-indicated side faces of the rotary plate 32. This distal end portion of the arm 24 has a rounded corner 48 having a radius slightly larger than the distance between the mounting rod 28 and the detent protrusion 46, and an extension 50 which extends sideways from one of the opposite side faces thereof remote from the rounded corner 48 so as to form the other corner. In this arrangement, the detent protrusion 46 of the rotary plate 32 may pass over the rounded corner 48 of the arm 24 due to the elastic deformation of the detent protrusion 46, only when the lens holder 30 is manually rotated by the user from a horizontal position (FIG. 3) to a vertical position (FIG. 4) or vice versa. The detent protrusion 46 is prevented from passing over the extension 50 of the arm 24 even if the user further rotates the lens holder 30.

Thus, the lens holder 30 may be rotated within a substantial range of 90° with the detent protrusions 46 moved along the respective rounded corners 48 of the support member 20. However, the lens holder 30, while it is not being rotated by the user, is held selectively in the horizontal position (FIG. 3) in which the holder 30 has a horizontal posture perpendicular to the axial direction of the container body 12, or the vertical position (FIG. 4) in which the holder 30 has a vertical posture parallel to the axial direction of the body 12. In this case, the contact lenses are positioned in the lens storage chambers of the lens holder 30, to have a horizontal attitude in which the axes of the lenses are parallel to the axial direction of the container body 12 when the lens holder 30 is held in the horizontal position, and a vertical attitude in which the axes of the lenses are perpendicular to the axial direction of the body 12 when the lens holder 30 is held in the vertical position.

In the instant embodiment, the detent protrusions 46 of the rotary plate 32, the rounded corners 48 and extensions 50 of the support member 20 constitute detent means for preventing the lens holder from freely rotating in the enclosed space, and for holding the lens holder 30 selectively in the above-indicated horizontal or vertical position.

Figure 4:
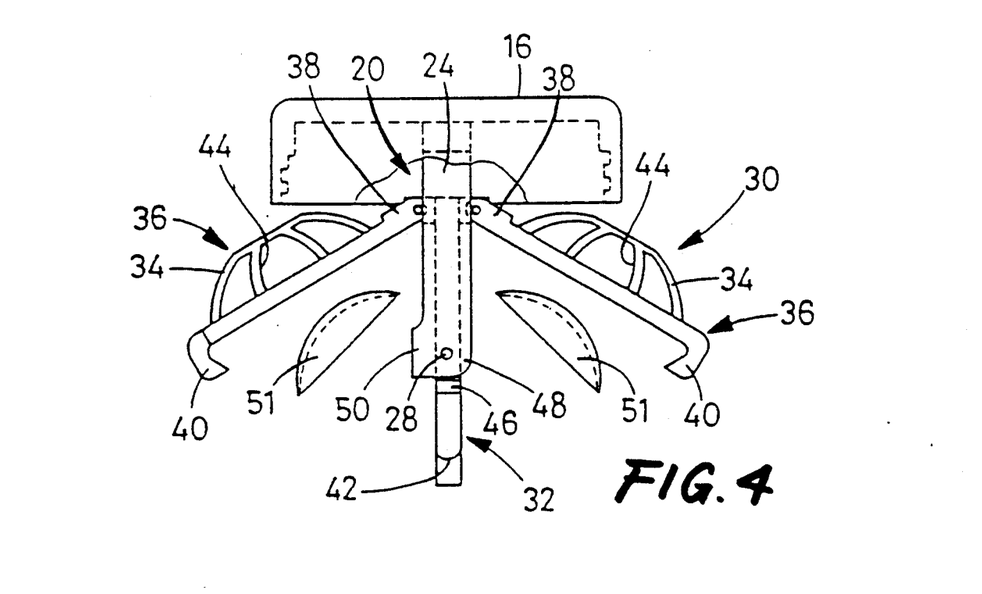
FIG. 4 is a side elevational view showing the lens case of FIG. 1, in which the lens holder is held in the vertical position with pivotable members placed in their open positions.

There will be described a manner of cleaning a pair of contact lenses 51 by using the contact lens case 10 constructed as described above. Initially, the lens holder 30 is manually rotated to the vertical position as shown in FIG. 4, and is held in this position by the detent means (46, 48, 50) described above. In this condition, the support member 20 and the cap member 16 do not interfere with pivotal movement of the pivotable members 36, 36, and thus permit the pivotable members 36 to be widely opened, whereby the contact lenses 51 can be easily put into and taken out of the basket portions 34 of the members 36.

After the contact lenses 51 are placed in the respective basket portions 34, the pivotable members 36 are placed in the closed positions, and the lens holder 30 is manually rotated back to and held in the horizontal position as shown in FIG. 3. In this particular embodiment, if the user forgets to rotate the lens holder 30 to the horizontal position, the lens holder 30 is adapted to hit the bottom wall of the container body 12, thereby preventing the cap member 16 from being screwed on the body 12 while the lens holder 30 is held in the vertical position. Thus, the user is notified of his or her error.

Then, the cap member 16 is screwed onto the container body 12 into which a given amount of cleaning liquid has been poured, so that the cap member 16 and the container body 12 are fluid-tightly fixed to each other with the lens holder 30 accommodated in the enclosed space defined therebetween. To allow good flows of the liquid within the contact lens case 10, the amount of the cleaning liquid poured into the case 10 is held in a range of several milliliters to a value slightly smaller than the inner volume of the case 10. More preferably, the amount of the liquid poured is about a half the volume of the case 10.

The contact lens case 10 containing the contact lenses 51 and the cleaning liquid is then gripped by one hand, and is shaked in the axial direction or repeatedly inverted in the opposite directions. As a result, the cleaning liquid in the case 10 is caused to intensely flow in the axial direction of the container body 12, to thereby clean the contact lenses 51 with the flowing liquid. In this respect, since the lens holder 30 is placed in the horizontal position as shown in FIG. 3, the contact lenses 51 accommodated in the holder 30 are positioned to have a horizontal attitude which is perpendicular to the direction of flows of the cleaning liquid. Accordingly, the cleaning liquid flowing in the case 10 is effectively applied to the opposite major surfaces of the lenses 51, assuring an excellent effect of cleaning the lenses 51.

Upon completion of the cleaning operation as described above, the cleaning liquid is discharged from the contact lens case 10. Then, a suitable liquid for rinsing the contact lenses 51 is poured into the lens case 10, and the lens case 10 is shaked so as to rinse the lenses 51. After the rinsing is finished, the lens case 10 is filled with a suitable liquid for storing the lenses 51.

When the contact lenses 51 are taken out of the lens holder 30, the holder 30 is manually rotated to the vertical position as shown in FIG. 4, so that the lenses 51 become more accessible to the user.

The contact lens case 10 of the instant embodiment is also advantageous where soft contact lenses are boiled for the purpose of disinfection. Namely, since the lens holder 30 is detachable from the support member 20, the lens holder 30 with the lenses accommodated therein can be moved into a suitable device so that the lenses may be boiled and disinfected within the device.

As is understood from the above description, the use of the instant contact lens case 10 makes it easy to effect a sequential procedure of cleaning, rinsing and storing the contact lenses 51, and to disinfect soft contact lenses by boiling. Further, since the pivotable members 36 of the lens holder 30 are allowed to pivot by a relatively large angle with respect to the rotary plate 32, the contact lenses 51 can be put into and taken out of the basket portions 34 of the pivotable members 36 with improved handling ease and accessibility. Moreover, the contact lens case 10 is simple in construction, and therefore less likely to be broken. When the contact lenses 51 are cleaned by shaking the lens case 10, the lenses 51 may be effectively exposed to the cleaning liquid which flows in the case 10 in the direction perpendicular to the surfaces of the lenses 51, resulting in a significantly improved effect of cleaning the lenses 51. Namely, the cleaning liquid flowing in the case 10 is effectively applied to the opposite major surfaces of the lenses 51 having a horizontal attitude. Furthermore, the instant contact lens case 10 is applicable to both hard contact lenses and soft contact lenses.

While there has been described one embodiment of the contact lens case of the present invention, there will be hereinafter described one embodiment of a lens treating device of the present invention, which uses the lens case as described above to more effectively clean contact lenses.

Figure 5:
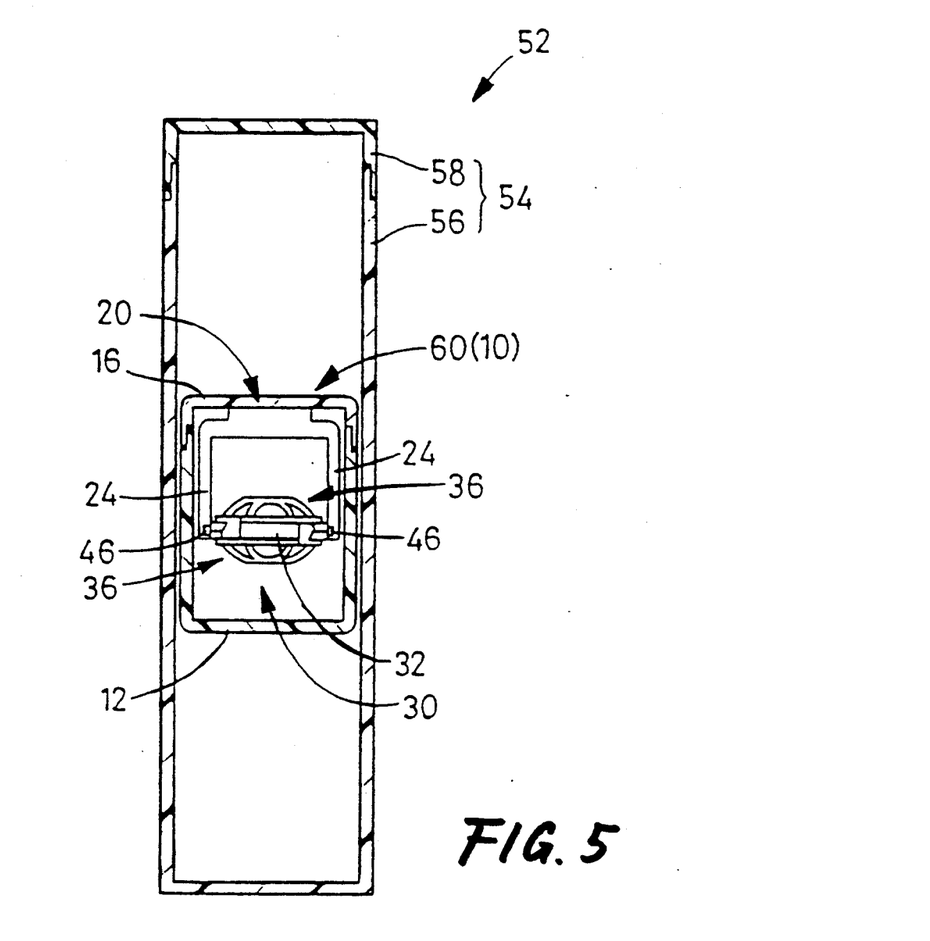
FIG. 5 is an elevational view in longitudinal cross section showing a lens treating device for treating contact lenses as one embodiment of the present invention.

Referring to FIG. 5, there is shown a lens treating device 52 constructed according to the present invention. In FIG. 5, reference numeral 54 denotes an elongate cylindrical outer case which consists of a cylindrical body 56 closed at one axial end, and a lid 58 removably screwed on the other axial end portion of the cylindrical body 56 so as to close the opening of the body 56. Thus, an enclosed space is formed in the outer case 54. In the enclosed space of the outer case 54, there is accommodated an inner case 60 having a length which is about one third of that of the outer case 54, such that the inner case 60 is axially slidable within the outer case 54. The cylindrical body 56, the lid 58 and the container body 12 of the inner case 60 are all formed of a transparent synthetic resin, so that the contact lenses stored in the inner case 60 can be observed from the outside of the lens treating device 52.

While the cylindrical body 56 and the lid 58 of the outer case 54 are fixed together by screwing in the instant embodiment, other means may be employed for fixing these members 56, 58 together, provided the lid 58 is not detached from the cylindrical body 56 even if the the inner case 60 collides against the lid 58. For example, the lid 58 may be press-fitted on the cylindrical body 56 with a single action, by means of elasticity of one or both of these members 56, 58.

The inner case 60 is identical in construction with the contact lens case 10 of the preceding embodiment. Namely, the inner case 60 includes the container body 12, cap member 16, support member 20, lens holder 30 and detent means (46, 48, 50). The lens holder 30 is rotatable within a range of 90° with respect to the support member 20, and can be held by the detent means selectively in the horizontal or vertical position. The inner case 60, in which are accommodated contact lenses and a suitable amount of cleaning liquid, is axially slidingly reciprocated within the outer case 54, so that the contact lenses may be cleaned due to the liquid flows caused by the reciprocating movement of the case 60.

Accordingly, the lens treating device 52 employing the inner case 60 is advantageous in that the contact lenses can be easily put into and taken out of the case 60 with excellent handling ease while the lens holder 30 is held in the vertical position, and in that the contact lenses are effectively exposed to the cleaning liquid during a cleaning operation, assuring a further improved cleaning effect, while the lens holder 30 is held in the horizontal position.

The cleaning operation by use of the lens treating device 52 is effected only by axially shaking or repeatedly inverting the outer case 54 in which the inner case 60 is accommodated, so that the inner case 60 is axially slidingly reciprocated or shuttled between the axially opposite end walls of the outer case 54. In this case, the inner case 60 is moved a relatively large distance in each stroke, compared to the actual distance of movement of the outer case 54 which is obtained by the shaking by the user. Further, the inner case 60 hits against the axially opposite end walls of the outer case 54 during its reciprocating movement. Consequently, considerably efficient and intensive flows of the cleaning liquid will occur within the inner case 60, assuring a significantly improved effect of cleaning the contact lenses stored in the inner case 60. Therefore, the use of the lens treating device 52 makes it possible to effectively remove stains from contact lenses, even if the lenses are stained with oily substances, such as cosmetics, which are difficult to remove.

Referring next to FIGS. 6 through 11, there will be described another embodiment of the contact lens case of the present invention. In the following description, the same reference numerals as used in the preceding embodiments will be used to identify structurally and/or functionally corresponding elements, and no detailed description of these elements will be provided.

Figure 6:
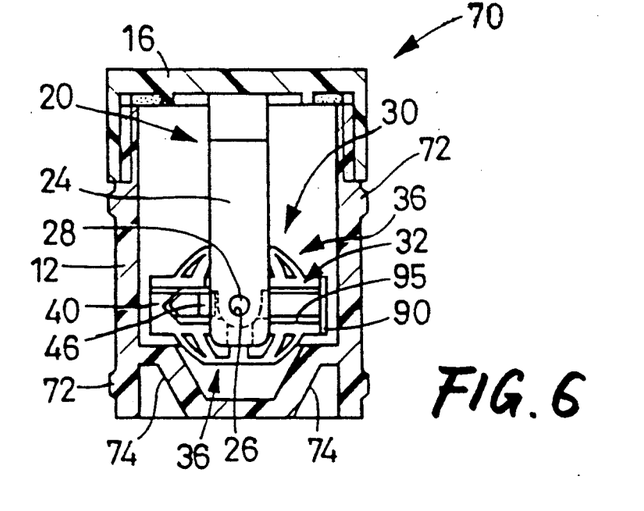
FIG. 6 is an elevational view in longitudinal cross section showing a contact lens case as another embodiment of the present invention.
Figure 7:
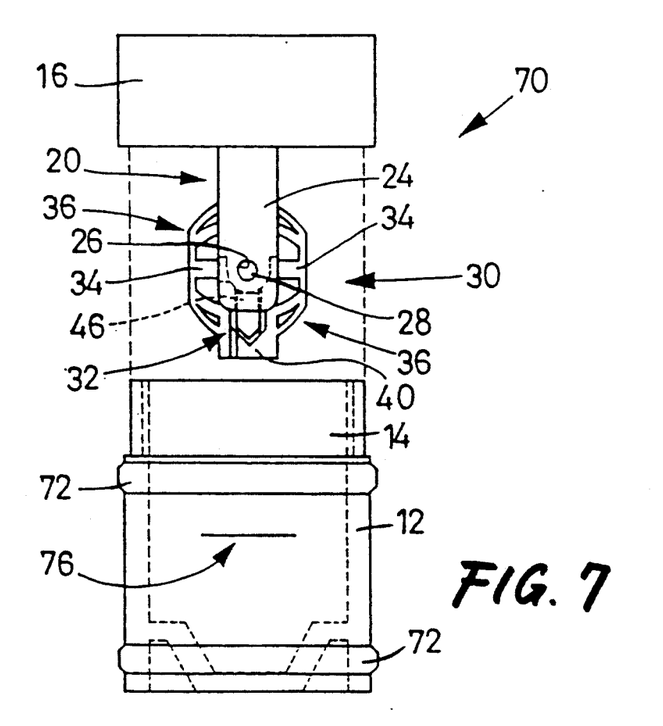
FIG. 7 is a view showing the contact lens case of FIG. 6 when a cap member with a lens holder is detached from a container body.

In a contact lens case 70 as shown in FIGS. 6 and 7, the container body 12 has two annular lips 72, 72 formed on the outer circumferential surface of the cylindrical wall thereof at its upper and lower end portions, respectively. These annular lips 72 are effective to reduce resistance to the sliding movement of the lens case 70 and to prevent the outer surface of the lens case 70 from being bruised or excessively rubbed, when the lens case 70 is slidden within an outer case 80 (which will be described later) during a cleaning operation. Further, the container body 12 of the lens case 70 is formed with a bottom wall having a raised peripheral portion 74, so that the required amount of the cleaning liquid or other treating liquid can be effectively reduced. In addition, the cylindrical wall of the container body 12 is provided with an indication 76 representative of a desired water level, as shown in FIG. 7, so that the amount of the liquid necessary to treat the lenses at one time can be considerably easily recognized.

Figure 8:
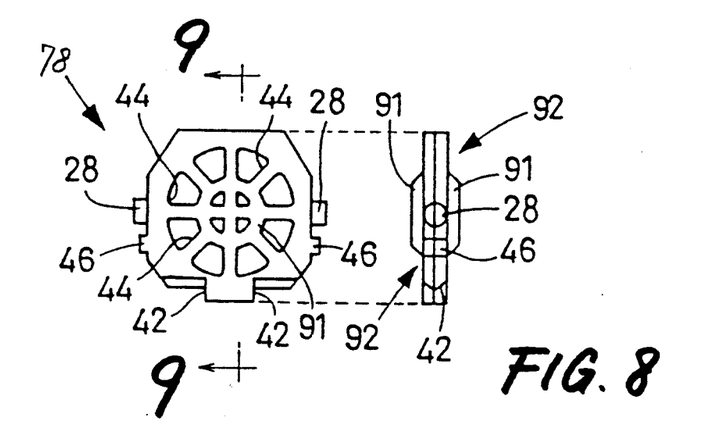
FIG. 8 is a plan view and a right-hand side view both showing a rotary structure of the lens holder of the lens case of FIG. 6.
Figure 9:
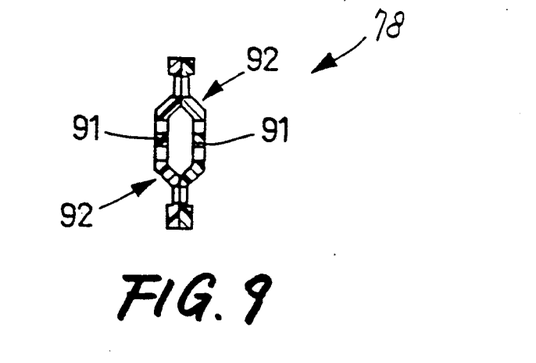
FIG. 9 is a cross sectional view taken along line 9—9 of FIG. 8.
Figure 10:
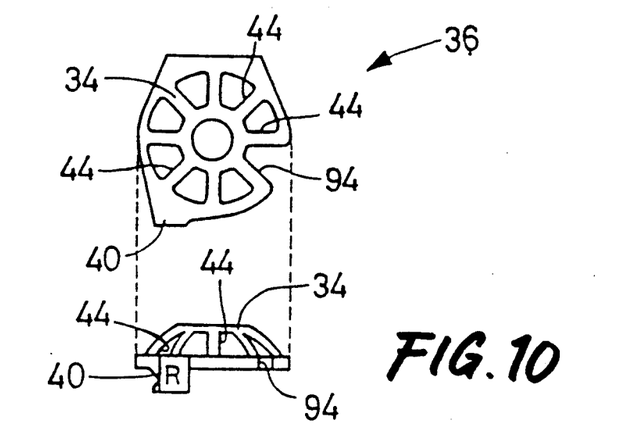
FIG. 10 is a plan view and a front view both showing a pivotable member of the lens holder of the lens case of FIG. 6.

On the other hand, the lens holder 30 accommodated in the lens case 70 has a rectangular rotary structure 78 as shown in FIGS. 8 and 9, and the pivotable members 36 as shown in FIG. 10. The pivotable members 36 are connected to the rotary structure 78 by an elastic connecting member 90 (FIG. 6) so that the members 36 are pivotably disposed on the opposite major surfaces of the rotary structure 78. As shown in FIG. 9, the rotary structure 78 consists of two rectangular plates 92, 92 each having a convex center portion 91 which is shaped to follow a concave inner surface of a contact lens to be disposed thereon. These rectangular plates 92 are bonded together at their peripheral portions such that the convex center portions 91 protrude from the opposite major surfaces of the rotary structure 78. Accordingly, the shape of the lens storage chamber defined between the rotary structure 78 and the basket portion 34 of each pivotable member 36 substantially corresponds to the shape of the contact lens to be stored in the chamber. When the instant contact lens case 70 is shaked with contact lenses stored in the lens storage chambers of the lens holder 30 as described above, the contact lenses may hit against the basket portions 34 of the pivotable members 36 of the lens holder 30, and against the convex center portions 91 of the rotary structure 92. Thus, the lenses can be cleaned with significantly improved efficiency, not only due to flows of a cleaning or other liquid applied to the surfaces of the lenses, but also due to collision or contact of the lenses with these portions 34, 91 of the lens holder 30.

As shown in FIG. 10, a cutout 94 is formed through the basket portion 34 of each pivotable member 36 of the lens holder 30, so as to make it easy to pick up the contact lens by fingers or forceps when the lens is put into or taken out of the basket portion 34. Further, the catches 40 of the pivotable members 36 are provided with symbols "R" and "L", respectively, so as to permit the user to place the contact lenses for right and left eyes in the appropriate pivotable members 36 without fail, and to allow easy recognition of the lenses already stored in the pivotable members 36. In the lens holder 30 of the instant lens case 70, the catches 40 of the pivotable members 36 are adapted to engage the corresponding cutouts 42 of the rotary structure 78, such that a slight gap 95 is formed between the rotary structure 78 and each pivotable member 36 when it is placed in the closed position as shown in FIG. 6. This arrangement prevents the contact lens from being broken even when the lens is erroneously nipped between the pivotable member 36 and the rotary structure 78 upon closing of the member 36.

The instant contact lens case 70 further includes detent means provided between the lens holder 30 and the support member 20 for holding the lens holder 30 selectively in the horizontal position as shown in FIG. 6 or the vertical position as shown in FIG. 7. Namely, the lens holder 30 is held in the horizontal position while the contact lenses stored in the holder 30 are cleaned, and is held in the vertical position when the lenses are put into or taken out of the lens holder 30.

Figure 11:
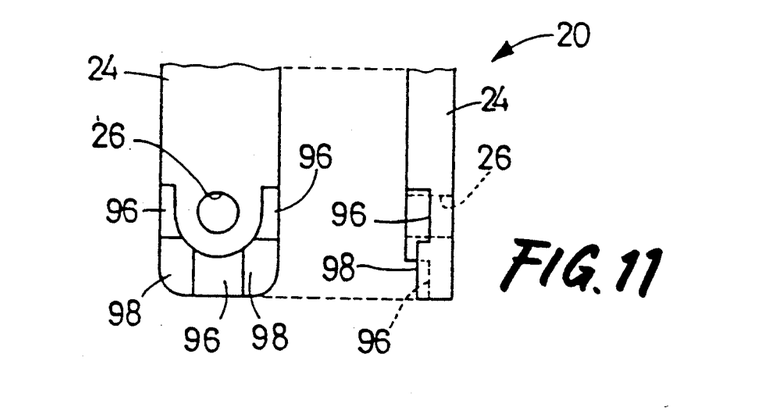
FIG. 11 is an enlarged fragmentary view showing an end portion of an arm of a support member of the lens case of FIG. 6, as seen from two different sides.
Figure 12:
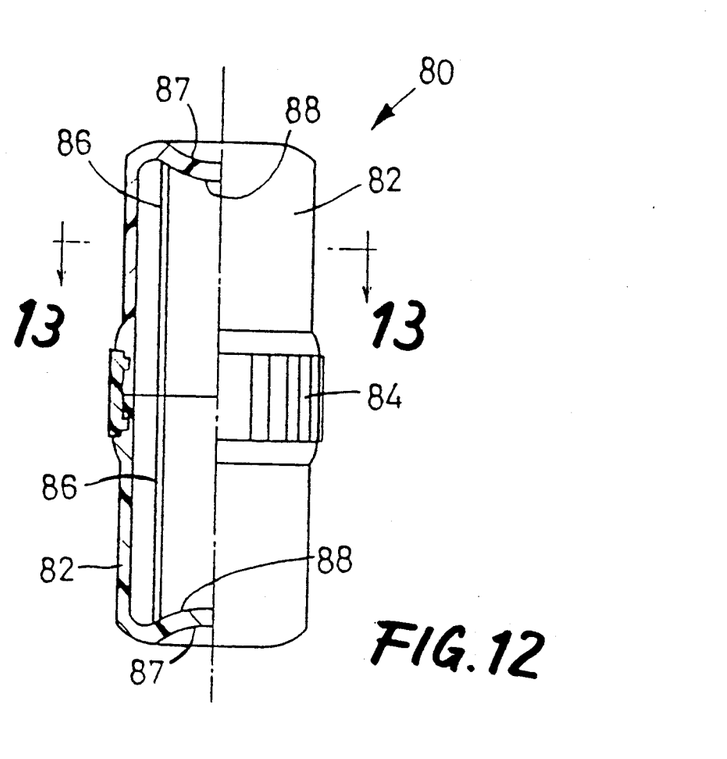
FIG. 12 is a view showing a modified form of an outer case used for the lens treating device of the invention, the left half being a longitudinal cross sectional view and the right half being a front elevational view.
Figure 13:
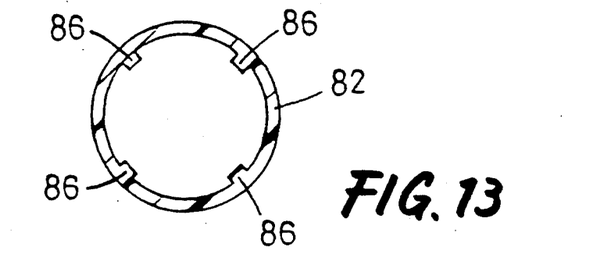
FIG. 13 is a cross sectional view taken along line 13—13 of FIG. 12.

More specifically described, the lens holder 30 is provided with two detent protrusions 46, 46 which are formed on the side faces of the rotary structure 32 on which the mounting rods 28 are formed, such that the detent protrusions 46 are spaced a suitable distance from the corresponding rods 28. On the other hand, each of the two arms 24 of the support member 20 has three recesses 96 formed in the inner side face of the distal end portion thereof, for receiving the corresponding detent protrusion 46 of the rotary structure 32. As shown in FIG. 11, the recesses 96 include two opposite upper recesses and a lower recess, which are arranged so as to surround the relevant through-hole 28 for receiving the mounting rod 28 of the rotary structure 32. Each arm 24 of the support member 20 also has two stepped portions 98 formed between the lower recess 96 and the upper recesses 96, 96, respectively. The height of the stepped portions 98 is determined so that the detent protrusion 46 can pass over the stepped portions 98 based on elastic deformation of the arm 24.

When the lens holder 30 is manually rotated by the user, therefore, the detent protrusions 46 of the rotary structure 32 are caused to pass over the stepped portions 98 of the support member 20, so that the detent protrusions 46 can be moved between the adjacent ones of the recesses 96 of the support member 20. Thus, the lens holder 30 can be rotated within a range of 180°. In this case, either one of the pivotable members 36 may be located below the other member 36 when the lens holder 30 is placed in the horizontal position. Further, the lens holder 30 is never rotated to a position where the pivotable members 36 are open toward the cap member 16. With the detent protrusions 46 of the rotary structure 78 received in any one of the recesses 96 of the arms 24, the lens holder 30 is fixed in the corresponding one of the vertical and horizontal positions. Thus, in the instant embodiment, the detent protrusions 46, recesses 96 and stepped portions 98 constitute the detent means for holding the lens holder 30 selectively in the horizontal or vertical position.

In the contact lens case 70 constructed as described above, the contact lenses can be easily put into and taken out of the lens holder 30 with improved handling ease, while the lens holder 30 is held in the vertical position. Further, the cleaning of the contact lenses is effected while the lens holder 30 is held in the horizontal position, so that the cleaning liquid is effectively applied to the opposite major surfaces of the contact lenses, to thereby provide an improved cleaning effect.

Referring next to FIGS. 12-16, there is shown outer case 80 which accommodates the contact lens case 70 as an inner case to provide a lens treating device as another embodiment of the invention. The outer case 80 consists of a cylindrical body in the form of a connector ring 84 and two cylindrical lid members 82, 82 each closed at one axial end. The outer case 80 is assembled such that the open ends of the lid members 82 are butted together and fitted in the connector ring 84. A plurality of axially extending ribs or rails 86 are formed integrally on the inner circumferential surface of the outer case 80, so as to effectively reduce resistance to the sliding movement of the lens case 70 and to prevent the outer surface of the lens case 70 from being bruised or excessively rubbed, when the lens case 70 is slidden within the outer case 80. Further, each of the two lid members 82 of the outer case 80 has a bottom wall having a concave outer surface 87 and a convex inner surface 88. In this case, the outer case 80 may be easily gripped at the axially opposite concave outer surfaces 87 of the lid members 82. The convex inner surfaces 88 of the bottom walls of the lid members 82 serve to reduce an area of collision between the outer case 80 and the lens case 70, thereby effectively reducing noise caused by the collision, while preventing both of the cases 70, 80 from being bruised or damaged.

Figures 14, 15:
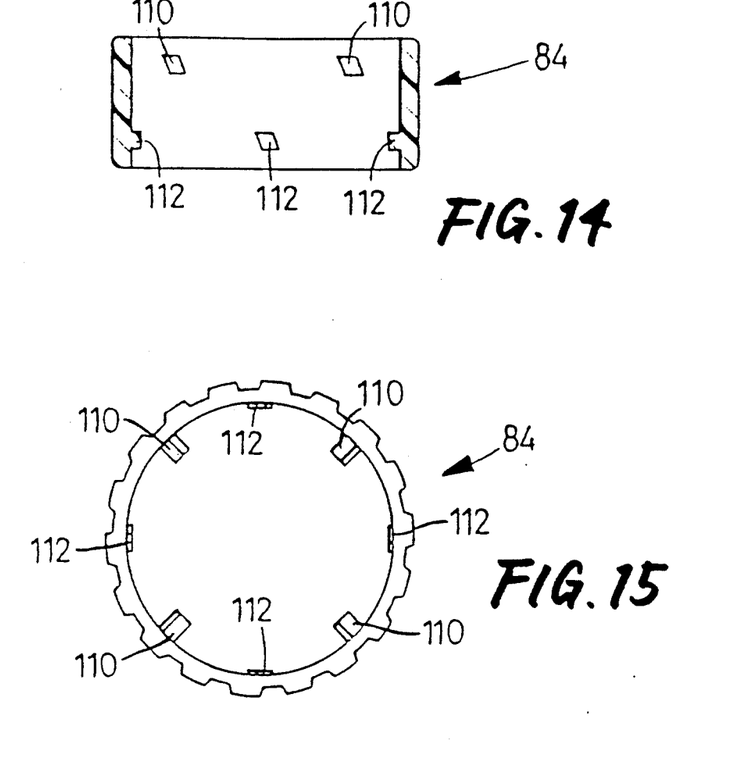
FIG. 14 is a cross sectional view showing a connector ring which is adapted to engage two lid members to provide the outer case of FIG. 12.
FIG. 15 is a plan view showing the connector ring of FIG. 14.
Figure 16:
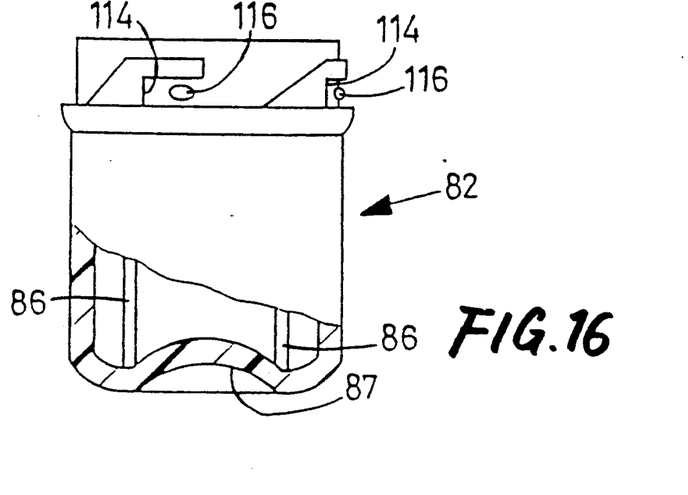
FIG. 16 is a partially cutaway front view showing one of the two lid members of the outer case of FIG. 12.

As shown in FIGS. 14 and 15, the connector ring 84 has relatively high four pawls 110 formed on one axial end portion of the inner circumferential surface thereof, and relatively low four pawls 112 formed on the other axial end portion thereof. The pawls 110, 112 are equally spaced from each other and arranged alternately in the circumferential direction of the ring 84, as shown in FIG. 15. On the other hand, each of the lid members 82 has four engaging grooves 114 for receiving the pawls 110, 112 of the ring 84, as shown in FIG. 16. These grooves 114 are formed on the outer circumferential surface of the open end portion of the lid member 82, such that the grooves 114 are equally spaced from each other in the circumferential direction of the member 82. At the inlet portion of each groove 114, there is formed an engaging boss 116 adapted to engage the corresponding one of the pawls 110, 112 of the connector ring 84. In this arrangement, when the lid members 82, 82 are rotated relative to the connector ring 84, the pawls 110, 112 of the ring 84 pass over the engaging bosses 116, and are inserted into the respective grooves 114 of the members 82. Thus, the connector ring 84 is assembled with the lid members 82, to thereby provide the outer case 80. When the two lid members 82 are rotated in the reverse directions so as to disassemble the outer case 80, only one of the members 82 which engages the relatively low pawls 112 is first disengaged from the connector ring 84, because of the difference in the height between the pawls 110 and the pawls 112. In other words, the two lid members 82, 82 are favorably prevented from being disengaged from the connector ring 84 at the same time.

The use of the thus constructed outer case 80 for the lens treating device makes it possible to remarkably intensify the flows of a cleaning liquid or other liquid in the contact lens case 70 which is slidden within the outer case 80, assuring an effectively improved effect of cleaning the lenses.

When a lens treating device 52 constructed as shown in FIG. 5 was actually used to clean contact lenses which were stained with eye shadow (cosmetics), the stains (eye shadow) were completely removed from the lenses. The outer and inner case 54, 60 and lens holder 30 of the lens treating device 52 used for the test were dimensioned as indicated below. The inner case 60 was filled with 5 ml of a cleaning liquid (available from Menicon Co. Ltd., MENICLEAN). To clean the contact lenses, the treating device 52 was axially shaked up and down about 20 times with the outer case 54 gripped by a hand.

(a) outer case
Outside diameter: 33 mm  Inside diameter: 29 mm
Wall thickness: 2 mm     Overall length: 104 mm
(b) inner case
Outside diameter: 26 mm  Inside diameter: 22 mm
Wall thickness: 2 mm     Overall length: 34 mm
(c) lens holder
Largest diameter of semispherical recess of basket portion: 16 mm
Depth of semispherical recess of basket portion: 5 mm -continued

| Wall thickness of rotary plate and pivotable members: 1 mm |
| --- |

The lens holder 30 was supported such that the lower surface of the holder 30 is spaced by 5 mm from the lower wall of the inner case 60, while the upper surface of the holder 30 is spaced by 10 mm from the upper wall of the inner case 60.

While some embodiments of the contact lens case and lens treating device of the present invention have been described in detail, for illustrative purpose only, it is to be understood that the invention is not limited to the details of these embodiments, but may be otherwise embodied with various other changes, modifications and improvements, which may occur to those skilled in the art, without departing from the scope of the present invention as defined in the appended claims. For example, the lens holder of the contact lens case does not necessarily have two lens storage chambers as in the illustrated embodiments, but may have one or three or more chambers for accommodating contact lenses. Further, the detent means for holding the lens holder in one of the vertical and horizontal positions is not limited to those as illustrated above.

What is claimed is:

1. A contact lens case for accommodating a contact lens, comprising:
   a cylindrical container body closed at one axial end, for receiving a liquid for treating the contact lens;
   a cap member removably attached to the other axial end of said container body to fluid-tightly close an opening of the body, so that an enclosed space is defined between said cap member and said container body;
   a support member which is attached at one end thereof to the inside of said cap member, and which extends from said cap member into said enclosed space in an axial direction of said container body;
   a lens holder rotatably supported at the other end of said support member and accommodated in said enclosed space, said lens holder comprising a plate member and at least one cover forming at least one lens storage chamber each for receiving the contact lens, said lens holder having a plurality of through-holes which permit said liquid to flow therethrough; and
   detent means disposed between said lens holder and said support member for preventing said lens holder from freely rotating in said enclosed space, and for holding said lens holder selectively in a horizontal position in which said lens holder has a horizontal posture substantially perpendicular to said axial direction of said container body, or a vertical position in which said lens holder has a vertical posture substantially parallel to said axial direction of the container body, so that the contact lens received in said at least one lens storage chamber has a horizontal attitude substantially perpendicular to said axial direction of the container body when said lens holder is held in said horizontal position, and a vertical attitude substantially parallel to said axial direction of the container body when said lens holder is held in said vertical position.

2. A contact lens case according to claim 1, wherein said plate member consists of a generally rectangular rotary member, and said at least one cover consists of two pivotable members which are pivotably disposed on opposite major surfaces of said rotary member, each of said two pivotable members having a basket portion formed at a central part thereof, said rotary member cooperating with said basket portions of said two pivotable members to define therebetween two lens storage chambers as said at least one lens storage chamber.

3. A contact lens case according to claim 2, wherein said rotary member has two mounting rods formed on opposite side faces thereof, and said support member has two arms having respective holes formed in distal end portions thereof, said two mounting rods being inserted in said holes of said support member so that said lens holder is rotatably supported by said support member.

4. A contact lens case according to claim 3, wherein said detent means comprises two protrusions formed on said opposite side faces of said rotary member, respectively, and a rounded corner and an extension which are formed at each of said distal end portions of said two arms of said support member such that said rounded corner and said extension are opposite to each other with respect to a corresponding one of said holes of said support member.

5. A contact lens case according to claim 3, wherein said detent means comprises two protrusions formed on said opposite side faces of said rotary member, respectively, and three recesses and two stepped portions which are formed alternately at each of said distal end portions of said two arms of said support member so as to surround a corresponding one of said holes of said support member.

6. A contact lens case according to claim 2, wherein said rotary member consists of two rectangular plates having respective convex center portions which protrude therefrom in the opposite directions toward said basket portions of said pivotable members.

7. A contact lens case according to claim 1, wherein said container body has a bottom wall having a raised peripheral portion.

8. A lens treating device for treating a contact lens, comprising:
   an elongate cylindrical outer case having a cylindrical body which is open at at least one of opposite axial ends, and at least one lid removably attached to said cylindrical body to close said at least one axial end thereof; and
   a contact lens case, for accommodating a contact lens, as an inner case, for fluid-tightly receiving the contact lens and a liquid for treating the contact lens, said inner case being accommodated in said outer case such that said inner case is axially slidingly reciprocable within said outer case, whereby said liquid is forced to flow within said inner case so as to clean the contact lens, by a reciprocating movement of said inner case when said outer case is axially shaked or repeatedly inverted, said contact lens case comprising:
   a cylindrical container body closed at one axial end, for receiving a liquid for treating the contact lens;
   a cap member removably attached to the other axial end of said container body to fluid-tightly close an opening of the body, so that an enclosed space is defined between said cap member and said container body;
   a support member which is attached at one end thereof to the inside of said cap member, and which extends from said cap member into said enclosed space in an axial direction of said container body;

a lens holder rotatably supported at the other end of said support member and accommodated in said enclosed space, said lens holder comprising a plate member and at least one cover forming at least one lens storage chamber each for receiving the contact lens, said lens holder having a plurality of through-holes which permit said liquid to flow therethrough; and detent means disposed between said lens holder and said support member for preventing said lens holder from freely rotating in said enclosed space, and for holding said lens holder selectively in a horizontal position in which said lens holder has a horizontal posture substantially perpendicular to said axial direction of said container body, or a vertical position in which said lens holder has a vertical posture substantially parallel to said axial direction of the container body, so that the contact lens received in said at least one lens storage chamber has a horizontal attitude substantially perpendicular to said axial direction of the container body when said lens holder is held in said horizontal position, and a vertical attitude substantially parallel to said axial direction of the container body when said lens holder is held in said vertical position, said detent means holding said lens holder in said vertical position so that the contact lens received in said lens holder has said vertical attitude when the lens is put into or taken out of said lens holder, and holding said lens holder in said horizontal position so that the contact lens has said horizontal attitude during cleaning of the contact lens.

9. A lens treating device according to claim 8, wherein said cylindrical body of said outer case is closed at one axial end, said at least one lid consisting of a single lid which is removably fixed to the other axial end of said cylindrical body.

10. A lens treating device according to claim 8, wherein said outer case consists of two lid members as said at least one lid, and a connector ring as said cylindrical body which connects said two lid members.

11. A lens treating device according to claim 8, wherein said outer case has a plurality of axially extending ribs formed integrally on an inner circumferential surface thereof, for sliding contact with an outer circumferential surface of said inner case.

12. A lens treating device according to claim 8, wherein said inner case has a plurality of annular lips formed on an outer circumferential surface thereof, for sliding contact with an inner circumferential surface of said outer case.

* * * * *